United States Patent [19]

Fricke et al.

[11] Patent Number: 5,364,635
[45] Date of Patent: Nov. 15, 1994

[54] SOLID DRUG FORM WITH A HIGH VERAPAMIL CONTENT

[75] Inventors: Helmut Fricke, Mutterstadt; Thomas Moest, Moorrege; Ernst Flaig, Heidelberg, all of Germany

[73] Assignee: Knoll AG, Ludwigshafen, Germany

[21] Appl. No.: 97,057

[22] Filed: Jul. 27, 1993

Related U.S. Application Data

[60] Division of Ser. No. 891,921, Jun. 1, 1992, abandoned, which is a continuation of Ser. No. 590,138, Sep. 28, 1990, abandoned.

[30] Foreign Application Priority Data

Sep. 28, 1989 [DE] Germany .............................. 3932378

[51] Int. Cl.5 ............................................... A61K 9/16
[52] U.S. Cl. .................................... 424/451; 424/464; 424/465; 424/468

[58] Field of Search ................ 424/451, 464, 465, 468

[56] References Cited

U.S. PATENT DOCUMENTS

4,753,802  6/1988  Stephens et al. .................... 424/473
4,832,958  5/1989  Baudier .............................. 424/473

*Primary Examiner*—Thurman K. Page
*Assistant Examiner*—Raj Bawa
*Attorney, Agent, or Firm*—Oblon, Spivak, McClelland, Maier & Neustadt

[57] ABSTRACT

A solid drug form containing not less than 90% by weight verapamil is produced by granulating at from 30° to 55° C. with a little water, drying and, where appropriate, conventional tableting or by pelleting, in which case the granules obtained as described are, after cooling, moistened once again and compacted in a granulating mixer at from 30° to 55° C. and are dried.

12 Claims, No Drawings

SOLID DRUG FORM WITH A HIGH VERAPAMIL CONTENT

This is a division of application Ser. No. 07/891,921, filed on Jun. 1, 1992, and now abandoned which is a continuation of Ser. No. 07/590,138, filed on Sep. 28, 1990, and now abandoned.

The present invention relates to solid drug forms with a distinctly higher verapamil hydrochloride content than previously possible, and to processes for the production thereof.

"Verapamil" in the title and hereinafter always means verapamil hydrochloride. It is, of course, equally possible to use other pharmacologically accceptable salts in amounts appropriately modified from those in the claims.

The maximum content of verapamil in commercial verapamil tablets and cores of film-coated tablets is 70%. The highest concentration reported is just about 80% (EP-A 217 778). Higher concentrations cannot be attained because, in the granulating stage necessary before tableting, verapamil tends to become gummy in the granulating equipment and, even after drying, is difficult to form into tablets because this tendency also results in adhesion to the die of the tablet press. Direct tableting of commercial verapamil in high concentration (more than 70%) without previous granulation fails because of the poor flowability of the commercial raw material, the deficient binding ability despite the addition of readily deformable auxiliaries such as microcrystalline cellulose, and the tendency to become gummy and adhere under high compressive forces.

Because of the relatively large amounts of active compound and added auxiliaries required, verapamil tablets, especially tablets with a coating to delay release, are relatively large and thus unpleasant to swallow.

Hence it was an object of the present invention to develop smaller verapamil tablets, especially smaller delayed release verapamil tablets, or else smaller capsules filled with pellets, each of which contain the same amount of active compound. For this it was necessary to find a process for producing granules which have satisfactory flowability and a uniform small particle size and are readily formed into tablets, and pellets, each of which have a high verapamil concentration.

We have found that this object is achieved by solid drug forms with a verapamil content of not less than 90, preferably not less than 95 and, in particular, not less than 98, % by weight and processes for the production thereof. Solid drug forms within the meaning of the present invention are granules, pellets, tablets and fill-coated tablets. In the latter case, the abovementioned concentrations relate to the core of the tablets (without coating).

We have found, surprisingly, that verapamil granules which are outstandingly suitable for forming into tablets and have excellent flowability can be produced with little or no added auxiliaries and thus high content of active compounds, of up to 100%, in a straightforward manner by carrying out the granulation at from 30° to 55°, preferably 40° to 50° C., only with water (from 2 to 10, preferably 3 to 7, % by weight) or with water and small amounts of added release-delaying agent and/or binder, and that repetition of the procedure results in pellets of low porosity with a smooth surface and a diameter of from 0.3 to 1.5 mm, with the mean diameter and at least 70% by weight being in the range from 0.5 to 1 mm.

The maximum temperature is limited by the start of softening of the mixture. The effect according to the invention is gradually lost at below 30° to 40° C. The necessary energy input should preferably be provided entirely mechanically, but assistance from heating or introduction of warm (in place of cold) water is also possible.

It has emerged, unexpectedly to those skilled in the art, that granulation of commercial verapamil powder at elevated temperature results in a considerably smaller consumption of aqueous granulating medium (water or aqueous suspension or solution of auxiliary) than at normal temperature. Moreover, compaction in a conventional granulating mixer, preferably a high-efficiency granulator (high-speed mixing element, with or without a cutter, e.g. a Lödige vertical or horizontal granulator or Diosna, Colette, Henschel or Fielder granulator) takes place considerably more intensively than at room temperature and without the substance becoming gummy; the granules have a homogeneous particle size distribution so that not less than 70% by weight are within a 430 μm band within a particle size range of from 0.1 to 1 mm, preferably 0.2 to 1 mm. The granules which have been dried to a residual moisture content of 0.5% or less at from 30° to 50° C. in a conventional manner (cf. Handbooks of Pharmaceutical Technology) are equalized by screening without difficulty and without a tendency to become gummy. The process according to the invention can be used to produce even fine granules (not less than 80% by weight below 500 μm) without a large dust content (not more than 10% below 100 μm) very straightforwardly. In addition, the granules have exceptional flowability so that not less than 250, preferably not less than 300, grams flow through a DIN No. 8 cup in one minute. It is thus possible to use the granules according to the invention to produce microtablets, i.e. compressed pellets with a diameter of less than 2.5 mm, which are suitable for filling capsules (multi-unit dose).

The straightforward granulating and compaction process takes from 5 to 30, usually 10 to 15, minutes. During this time, the temperature of the product should rise into the range indicated above. Repetition of this process with the resulting granules which have been cooled, again adding from 2 to 10% water, until from 30° to 55° C. is again reached, results in the formation of the abovementioned pellets which are of low porosity compared with conventional pellets and have a smooth surface and a bulk density of from 0.5 to 0.7, preferably 0.55 to 0.65, g/ml and, above all, a verapamil content of previously unattained magnitude.

The pellets produced in this way contain about 3% water. This water can be substantially removed (i.e. down to about ≦0.5% residual moisture) by conventional drying processes as are described in all handbooks of pharmaceutical technology.

The nature of the binder is not critical it being possible to employ all conventional pharmaceutical binders such as gelatin, starch, casein, cellulose derivatives (e.g. methylcellulose, hydroxypropylmethylcellulose), shellac, polyglycols and polyvinylpyrrolidone in amounts of less than 10, preferably less than 5, in particular less than 2, % by weight based on verapamil.

It is also possible to employ a release-delaying agent in place of a binder or in addition thereto (up to a total amount of auxiliaries not exceeding 10% by. weight).

If added auxiliaries, besides a binder and/or release-delaying agent, are required for the tablet core, small amounts of conventional pharmaceutical lubricants and release agents such as magnesium stearate, stearic acid, glycerol tribehenate, Aerosil and talc suffice.

To delay release, the pellets or tablets are preferably coated with a release-delaying film. However, it is also possible to introduce small amounts (not exceeding 10% by weight) of release-delaying agent during the granulation. Suitable release-delaying materials for the fi$\mu$m coatings or for incorporation into the tablet are the conventional ones described in pharmacological textbooks, for example cellulose derivatives and copolymers of acrylic esters and their cationic and anionic derivatives (Eudragit E, R and S). They are applied dry, as organic solution or, preferably, as aqueous dispersion.

The essential advantages of the granules and pellets according to the invention may be summarized once again as follows:
1. They have a substantially uniform particle size.
2. They have a high strength so that they can undergo conventional processes for producing pharmaceutical forms without friability losses.
3. The low content or absence of auxiliaries and additives means that they can be used to produce small and compact and thus easy for patients to take) tablets, which may be film- or sugar-coated, or capsule fillings.
4. The pellets are substantially spherical with a smooth and low-porosity surface so that delay of release can be brought about very reproducibly with a very small amount of coating.

EXAMPLE 1

Production of Granules 2 kg of powdered verapamil were heated to 40° C. in a small, Jacketed high-efficiency granulator (UMC 12 mixer, Stephan & Söhne, Hameln, FRG). With maximumenergy input, 100 g of water at 40° C. was added within 30 sec, and granulation was continued until the temperature had risen to 50° C. (for about 5 min). After cooling, the initial granules had the following particle size distribution:

<100 $\mu$m<5%
<200 $\mu$m<13%
<430 $\mu$m>70%
<630 $\mu$m>85%
<750 $\mu$m>99%.

They were passed without difficulty through an oscillating screener (Frewitt S. A., Fribourg, Switzerland) with a 1.0 mm screen. The granules were dried to a 0.4% residual moisture in a circulating air oven at 40° C. and then passed without difficulty through an oscillating screener with a 0.63 mm screen; no clogging of the screen occurred. The flowability, measured in a DIN No. 8 cup, was 305 g/min.

The granules were mixed with 2% by weight talc and 1% by weight magnesium stearate and compressed to mechanically stable tablets which were easy to coat, and there was no tendency of the tablets to adhere to the sides of the die or faces of the punches.

The granules which had been passed through a 500 $\mu$m screen were compressed to microtablets which had a height of 2 mm and a diameter of 2 mm, with almost spherical convexities, which had high mechanical strength and low friability and which could be given a very effective release-delaying coating with relatively little diffusion-controlling lacquer in a fluidized bed or else in a perforated drum coater.

COMPARATIVE EXAMPLE

When 2 kg of verapamil are granulated in the small high-efficiency granulator of Example 1 under conventional conditions, i.e. at room temperature, using pure water, about 300 g are required for uniformwetting. The resulting granules cannot be passed through a 1.0 mm screen because an attempt leads to clogging and blockage. Even after wet screening through a 3 mm screen and conventional drying it is difficult to pass the granules through a 1 mm screen because even the dry granules tend to gum up the screen. Fine granules cannot be produced.

An attempt to compress granules of this type with the addition of small amounts of tableting auxiliaries (2% talc, 1% magnesium stearate) fails because pressure on the composition leads to immediate adhesion to the sides of the die and to the punches. Moreover, the resulting tablets are not bound together; they can be crushed between thumb and forefinger. It was possible to produce satisfactory tablets by including 20% lactose and 5% polyvinylpyrrolidone as binders in the granulating fluid, in each case proportions by mass of the dry granules. Furthermore, it was necessary to mix 5% microcrystalline cellulose with the composition before compression in order to reduce the tendency to adhesion. However, these conventional granules could not be used to produce microtablets 2 mm in diameter because the particle size could not be reduced sufficiently and the granules tended to adhere to the small punches after a short compression time so that some of the tablets were torn apart when the punches were retracted.

EXAMPLE 2

Production of Pellets 10 kg of verapamil hydrochloride were weighed into a 50 l mixer with a horizontal propeller and cutter (manufactured by Diosna, Osnabrück). With the mixer running, 0.5 kg of water at 27° C. was added. The process protocol is as follows:

| Process | Time [min] | Mixer setting | Cutter setting | Final temp. [°C.] |
|---|---|---|---|---|
| Start | 0 | — | — | 21.5 |
| Addition of water | 1 | 2 | 1 | 22.2 |
| Mixing | 20 | 2 | 2 | 45.0 |
| Cooling | 60 | — | — | 23.0 |
| Repetition of the moistening and mixing process | | | | |

The moisture content of the pellets at the end of the process was 3.0%. They were dried on trays in a circulating air oven with the inlet air at 40° C. until the residual moisture content was 0.3%.

The flowability of the pellets was measured after drying. The pellets flowed out of a DIN No. 8 cup in 14–15 sec, which corresponds to 235–250 g/min.

80% of the pellets had a particle size of from 0.5 to 0.8 mm. The bulk density of the pellets was 0.58–0.60 g/ml.

We claim:
1. A process for producing verapamil hydrochloride granules containing not less than 90% by weight verapamil hydrochloride, consisting essentially of the steps of:
mixing verapamil hydrochloride powder with 2–10% by weight water, an aqueous solution of a binder or release-delaying agent, or an aqueous suspension of a binder or release-delaying agent to form a mixture;

vigorously mixing and compacting said mixture for 5 to 30 minutes so that the temperature of said mixture rises to from 30°-55° C., and drying said compacted mixture to form granules having a particle size distribution such that not less than 70% by weight of said particles are within a 430 micron band within a particle size range of from 0.1 to 1 mm.

2. The process of claim 1, wherein said vigorous mixing and compacting is conducted until the temperature of said mixture rises to from 40°-50° C.

3. A process for producing verapamil hydrochloride granules containing not less than 90% by weight verapamil hydrochloride, consisting essentially of the steps of:

mixing verapamil hydrochloride powder with 2-10% by weight water, an aqueous solution of a binder or release-delaying agent or an aqueous suspension of a binder or release-delaying agent to form a mixture;

vigorously mixing and compacting said mixture for 5 to 30 minutes so that the temperature of said mixture rises to from 30°-55° C., drying said compacted mixture;

mixing said dried compacted mixture with 2-10% by weight water to form a second mixture;

vigorously mixing and compacting said second mixture for 5 to 30 minutes so that the temperature of said second mixture rises to from 30°-55° C. to form a second compacted mixture; and drying said compacted mixture to form granules having a particle size distribution such that not less than 70% by weight of said particles are within a 430 micron band within a particle size range of from 0.1 to 1 mm.

4. The process of claim 3, wherein said vigorous mixing and compacting is conducted until the temperature of said second mixture rises to from 40°-50° C.

5. The process of claim 1, wherein 3-7% by weight of said water, aqueous solution of a binder or release-delaying agent, or aqueous suspension of a binder or release-delaying agent is mixed with said verapamil hydrochloride powder.

6. The process of claim 1, wherein said compacted mixture is dried to a residual moisture content of 0.5% or less.

7. The process of claim 1, wherein said vigorous mixing and compacting step is conducted for a period of time ranging from 10-15 minutes.

8. The process of claim 3, wherein 3-7% by weight of said water, aqueous solution of a binder or release-delaying agent, or aqueous suspension of a binder or release-delaying agent is mixed with said verapamil hydrochloride powder.

9. The process of claim 3, wherein said compacted mixture is dried to a residual moisture content of 0.5% or less.

10. The process of claim 3, wherein said vigorous mixing and compacting step is conducted for a period of time ranging from 10-15 minutes.

11. A process for producing verapamil hydrochloride granules containing not less than 98% by weight verapamil hydrochloride, consisting essentially of the steps of:

mixing verapamil hydrochloride powder with 2-10% by weight water, an aqueous solution of a binder or release-delaying agent, or an aqueous suspension of a binder or release-delaying agent to form a mixture;

vigorously mixing and compacting said mixture for 5 to 30 minutes so that the temperature of said mixture rises to from 30°-55° C., and drying said compacted mixture to produce granules having a particle size distribution such that not less than 70% by weight of said particles are within a 430 micron band within a particle size range of from 0.1 to 1 mm.

12. A process for producing verapamil hydrochloride granules containing not less than 98% by weight verapamil hydrochloride, consisting essentially of the steps of:

mixing verapamil hydrochloride powder with 2-10% by weight water, an aqueous solution of a binder or release-delaying agent, or an aqueous suspension of a binder or release-delaying agent to form a mixture;

vigorously mixing and compacting said mixture for 5 to 30 minutes so that the temperature of said mixture rises to from 30°-55° C.;

drying said compacted mixture;

mixing said dried compacted mixture with 2-10% by weight water to form a second mixture;

vigorously mixing and compacting said second mixture for 5 to 30 minutes so that the temperature of said second mixture rises to from 30°-55° C.; and drying said compacted mixture to form granules having a particle size distribution such that not less than 70% by weight of said particles are within a 430 micron band within a particle size range of from 0.1 to 1 mm.

* * * * *